US009414668B2

(12) United States Patent
Worthington et al.

(10) Patent No.: US 9,414,668 B2
(45) Date of Patent: Aug. 16, 2016

(54) ORAL CARE IMPLEMENT

(71) Applicant: COLGATE-PALMOLIVE COMPANY, New York, NY (US)

(72) Inventors: Brian G. Worthington, Dunellen, NJ (US); Sharon Kennedy, Randallstown, MD (US); Eduardo Jimenez, Manalapan, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

(21) Appl. No.: 14/435,414

(22) PCT Filed: Oct. 26, 2012

(86) PCT No.: PCT/US2012/062127
§ 371 (c)(1),
(2) Date: Apr. 13, 2015

(87) PCT Pub. No.: WO2014/065817
PCT Pub. Date: May 1, 2014

(65) Prior Publication Data
US 2015/0265042 A1    Sep. 24, 2015

(51) Int. Cl.
*A46B 11/00* (2006.01)
*A61C 19/06* (2006.01)
(52) U.S. Cl.
CPC ........... *A46B 11/001* (2013.01); *A46B 11/0086* (2013.01); *A61C 19/063* (2013.01); *Y10T 29/49945* (2015.01)
(58) Field of Classification Search
CPC .................... A46B 11/0079; A46B 11/0086
USPC ............ 401/24, 202, 269; 215/317, 320, 321
See application file for complete search history.

(56) References Cited

U.S. PATENT DOCUMENTS 1,855,572 A * 4/1932 Gabriel .............. A46B 11/0041
401/166
4,106,152 A    8/1978 Hadary
(Continued)

FOREIGN PATENT DOCUMENTS

AU          44159      8/1980
CN        1352534      6/2002
(Continued)

OTHER PUBLICATIONS

International Search Report and the Written Opinion of the International Searching Authority issued in International Patent Application PCT/US2012/062127 mailed Jul. 31, 2013.

*Primary Examiner* — Mark A Laurenzi
*Assistant Examiner* — Joshua Wiljanen

(57) ABSTRACT

An oral care implement having an internal reservoir and improved leakage prevention. In one embodiment, the invention can be a toothbrush comprising: a handle (110) comprising an internal reservoir (140); a head coupled to the handle; an annular neck (180) extending from the handle, the annular neck having an inner surface (181) defining a passageway (182) into the internal reservoir; an end cap (150) comprising: a cap body (160) defining a cap socket (161) and comprising an annular wall (162) and an end portion (163); an annular plug wall (170) defining a central chamber (173), the annular plug wall protruding from the end portion into a cap socket to form an annular chamber (165) between an outer surface (172) of the annular plug wall and an inner surface (166) of the annular wall; and a first annular seal member (190) protruding from the outer surface of the annular plug wall; and the end cap coupled to the handle to seal the passageway in a fluid-tight manner.

20 Claims, 3 Drawing Sheets

(56) References Cited

U.S. PATENT DOCUMENTS

| | | |
|---|---|---|
| 4,124,316 A | 11/1978 | O'Rourke |
| 4,171,057 A | 10/1979 | Gach |
| 4,291,995 A | 9/1981 | Dikoff |
| 4,394,923 A | 7/1983 | Sugiyama |
| 4,582,075 A | 4/1986 | O'Neal et al. |
| 5,044,386 A | 9/1991 | Nelson |
| 5,173,983 A | 12/1992 | Le |
| 5,909,977 A | 6/1999 | Kuo |
| 5,979,680 A | 11/1999 | Farside |
| 6,129,474 A | 10/2000 | Mitchell et al. |
| 6,334,451 B1 | 1/2002 | Yang |
| 6,481,910 B1 | 11/2002 | Yang |
| 6,945,256 B2 | 9/2005 | Earl |
| 2002/0120991 A1 | 9/2002 | Cacka et al. |
| 2004/0007244 A1 | 1/2004 | Harms |
| 2008/0305010 A1 | 12/2008 | Anderson et al. |
| 2011/0103876 A1 | 5/2011 | Sylvester |
| 2011/0214240 A1 | 9/2011 | Jimenez et al. |
| 2012/0114410 A1 | 5/2012 | Jimenez et al. |

FOREIGN PATENT DOCUMENTS

| | | |
|---|---|---|
| FR | 1480395 | 5/1967 |
| JP | S51-122850 | 10/1976 |
| JP | S52-149869 | 12/1977 |
| JP | H01-150015 | 10/1989 |
| JP | H02-279108 | 11/1990 |
| JP | H09-240707 | 9/1997 |
| JP | 2006-151407 | 6/2006 |
| WO | WO2010/144938 | 12/2010 |
| WO | 2011/109626 A2 | 9/2011 |

* cited by examiner

ORAL CARE IMPLEMENT

CROSS-REFERENCE TO RELATED PATENT APPLICATIONS

This application is a U.S. national stage application under 35 U.S.C. §371 of PCT Application No. PCT/US2012/062127, filed Oct. 26, 2012, the entirety of which is incorporated herein by reference.

FIELD OF THE INVENTION

The present invention relates generally to oral care implements, and specifically to oral care implements having an end cap.

BACKGROUND OF THE INVENTION

Oral care implements, particularly toothbrushes, are typically used by applying toothpaste to a bristle section followed by brushing regions of the oral cavity such as the teeth, tongue and/or gums. Some oral care implements are equipped with built-in fluid reservoirs and systems for delivering dentifrice and other oral care agents to the bristle section of the oral care implement. There is a continuing need, however, for improved oral care implements for dispensing dentifrice and other oral care agents from the implement. Furthermore, there is a continuing need to improve the seal between the end cap and the handle of the oral care implement to reduce and/or eliminate dentifrice or other oral care agent leakage out of the fluid reservoir.

BRIEF SUMMARY OF THE INVENTION

The present invention is directed to an oral care implement having an internal reservoir and an end cap. In one aspect, the oral care implement includes a handle comprising the internal reservoir that contains an oral care fluid and a head coupled to the handle. An end cap is coupled to the handle in a manner that prevents leakage of the oral care fluid from the reservoir.

In one embodiment, the invention can be a toothbrush comprising: a handle extending along a handle axis from a proximal end to a distal end, the handle comprising an internal reservoir containing an oral care fluid; a head coupled to the distal end of the handle and having a plurality of tooth cleaning elements; an annular neck extending from the proximal end of the handle, the annular neck having an inner surface that defines a passageway into the internal reservoir of the handle; an end cap comprising: a cap body defining a cap socket, the cap body comprising an annular wall and an end portion; an annular plug wall having an inner surface defining a central chamber, the annular plug wall protruding from the end portion into the cap socket to form an annular chamber between an outer surface of the annular plug wall and an inner surface of the annular wall of the cap body; and a first annular seal member protruding from the outer surface of the annular plug wall; and the end cap coupled to the handle to seal the passageway in a fluid-tight manner such that the annular neck extends into the annular chamber, the annular plug wall extends into the passageway, and the first annular seal member biased into contact with an annular portion of the inner surface of the annular neck.

In another embodiment, the invention can be a toothbrush comprising: a handle extending along a handle axis from a proximal end to a distal end, the handle comprising an internal reservoir containing an oral care fluid; a head coupled to the distal end of the handle and having a plurality of tooth cleaning elements; an annular neck extending from the proximal end of the handle, the annular neck having an inner surface that defines a passageway into the internal reservoir of the handle; an end cap comprising: a cap body defining a cap socket, the cap body comprising an annular wall and an end portion; a plug protruding from the end portion into the cap socket to form an annular chamber between an outer surface of the plug and an inner surface of the annular wall of the cap body; and a first annular seal member between the outer surface of the plug and the inner surface of the annular wall of the cap body; and the end cap coupled to the handle to seal the passageway in a fluid-tight manner such that the annular neck extends into the annular chamber, the plug extends into the passageway, and the first annular seal member exerting pressure against an annular portion of the inner surface of the annular neck.

In yet another embodiment, the invention can be a method of sealing a passageway leading into an internal reservoir containing an oral care fluid that is located within a handle of a toothbrush, the method comprising: a) aligning an end cap with an annular neck extending from a proximal end of the handle of the toothbrush, the end cap comprising a cap body comprising an annular wall and an end portion that collectively define a cap socket, the annular neck having an inner surface that defines the passageway; and b) translating the annular neck into the cap socket until: (1) a plug of the end cap extends into the passageway; (2) the annular neck extends into an annular chamber formed between an outer surface of the plug and an inner surface of the annular wall of the cap body; and (3) a first annular seal member protruding from an outer surface of the plug exerts pressure against an annular portion of the inner surface of the annular neck, thereby forming a first annular hermetic seal.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
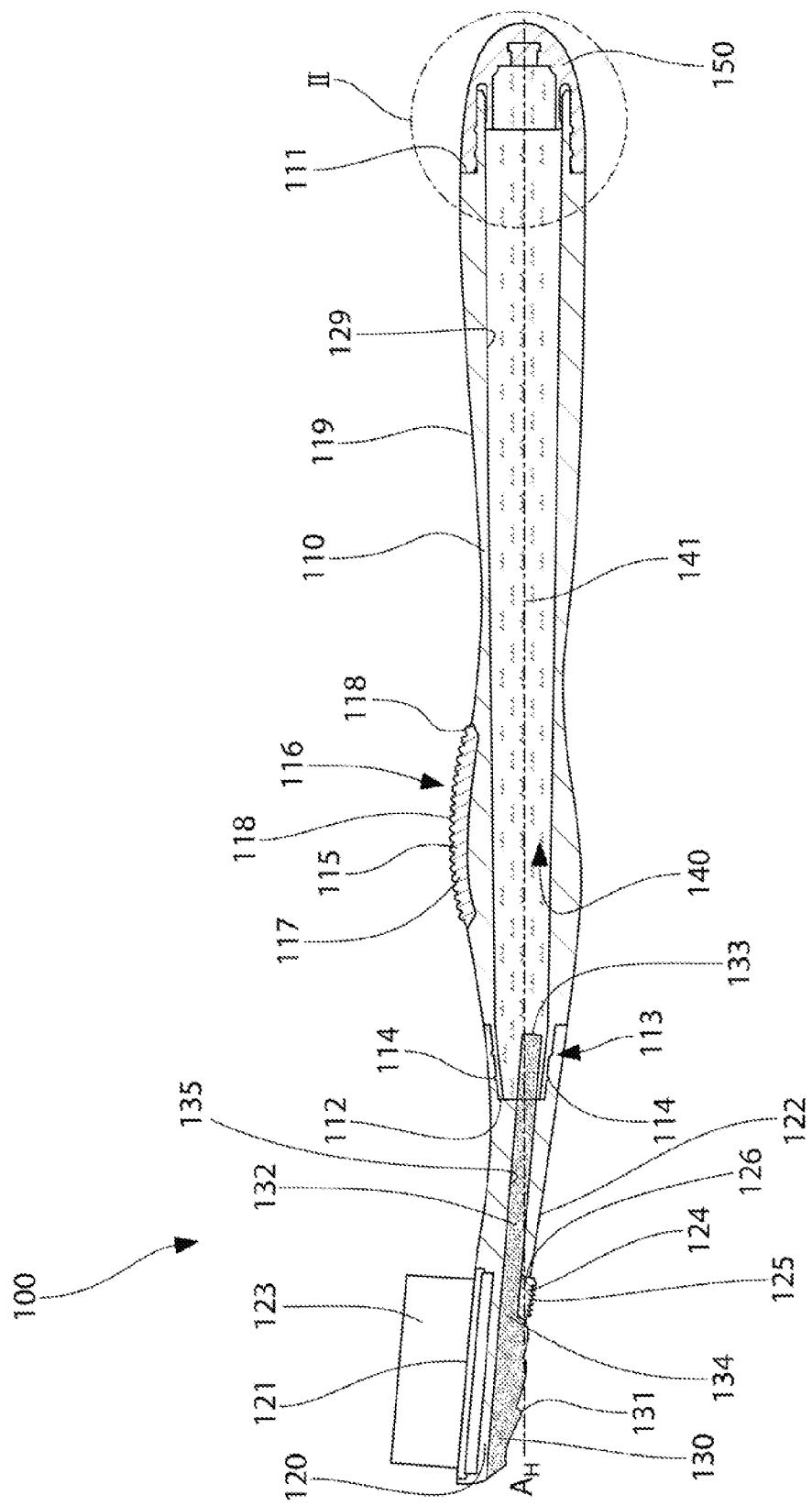
FIG. 1 is a cross-sectional view of an oral care implement in accordance with an embodiment of the present invention wherein the oral care implement comprises a handle having an internal reservoir and an end cap coupled to the handle.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above,"

"below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features, the scope of the invention being defined by the claims appended hereto.

Referring first to FIG. 1, an oral care implement 100 will be described in accordance with an embodiment of the present invention. In the exemplified embodiment, the oral care implement 100 is in the form of a manual toothbrush. However, in certain other embodiments the oral care implement 100 can take on other forms such as being a powered toothbrush, a tongue scraper, a gum and soft tissue cleanser, a water pick, an interdental device, a tooth polisher, a specially designed ansate implement having tooth engaging elements or any other type of implement that is commonly used for oral care. Thus, it is to be understood that the inventive concepts discussed herein can be applied to any type of oral care implement unless a specific type of oral care implement is specified in the claims.

The oral care implement generally comprises a handle 110 extending along a handle axis $A_H$-$A_H$ from a proximal end 111 to a distal end 112 and a head 120 coupled to the distal end 112 of the handle 110. Furthermore, an end cap 150 is coupled to the proximal end 111 of the handle 110 as will be discussed in more detail below. The end cap 150 extends along a cap axis $A_C$ (illustrated in FIGS. 2 and 3). The handle 110 is an elongated structure that provides the mechanism by which the user can hold and manipulate the oral care implement 100 during use. The handle 110 has a generic shape with various contours, none of which are specifically limiting of the present invention. Furthermore, the handle 110 also comprises an inner surface 129 that defines an internal reservoir 140 containing an oral care fluid 141 therein and an outer surface 119 that is gripped by a user during use of the oral care implement 100. The end cap 150 is coupled to the handle to prevent the oral care fluid 141 from leaking out of the internal reservoir 140.

In certain embodiments, the end cap 150 is removably coupled to the handle 110 so that the oral care fluid 141 contained within the internal reservoir 140 can be refilled upon depletion thereof. In such embodiments, with the end cap 150 removed from the handle 110 a user can refill the internal reservoir 140 with any desired oral care fluid 141, including the different types of oral care fluids discussed below. However, in certain other embodiments the end cap 150 may be permanently affixed to the handle 110. In such embodiments, upon depletion of the oral care fluid 141 the oral care implement 100 can either be used as a standard oral care implement 100 without the benefits of the oral care fluid 141, or the oral care implement 100 can be discarded.

In the exemplified embodiment, the internal reservoir 140 extends along the entire axial length of the handle 110 of the oral care implement. Thus, the internal reservoir 140 is capable of containing an amount of the oral care fluid 141 that is sufficient for multiple uses. Of course, in other embodiments the internal reservoir 140 may be smaller and only extend partially along the axial length of the handle 110. In certain such embodiments, the reservoir 140 may only include enough of the oral care fluid 141 for a single use of the oral care implement 100. In such embodiments, the oral care implement 100 can either be a disposable oral care implement that is discarded after one use, or the internal reservoir 140 can be refilled between uses as desired.

The oral care fluid 141 contained within the reservoir 140 is a material that provides oral health benefits to a user upon contact with a user's oral cavity. In one embodiment, the oral care fluid 141 is a fluidic material. For example, in certain embodiments the oral care fluid 141 is a mouthwash solution that cleans the oral surfaces when applied thereto and provides the user with breath freshening benefits. In other embodiments, the oral care fluid 141 is a tooth cleaning solution, such as a dentifrice. Of course, the oral care fluid 141 is not to be in any way limiting of the present invention and may include fluids having active or inactive agents that deliver therapeutic, cosmetic, experiential and/or sensorial benefits to a consumer during a tooth, soft tissue, tongue or interdental cleaning regimen. Specifically, the oral care material can be an anti-sensitivity agent, fluoride, a tartar protection agent, an antibacterial agent, an oxidative or whitening agent, an enamel strengthening or repair agent, a tooth erosion preventing agent, a tooth sensitivity ingredient, a gum health active, a nutritional ingredient, a tartar control or anti-stain ingredient, an enzyme, a sensate ingredient, a flavor or flavor ingredient, a breath freshening ingredient, an oral malodor reducing agent, an anti-attachment agent or sealant, a diagnostic solution, an occluding agent, a dry mouth relief ingredient, a catalyst to enhance the activity of any of these agents, colorants or aesthetic ingredients, arginine bicarbonate, chlorohexidine, triclosan, CPC, zinc oxide and combinations thereof. In certain embodiments, the oral care fluid 141 is free of a dentifrice as the oral care fluid 141 is intended to supplement traditional brushing of the teeth rather than supplant it (hence its delivery to the rear surface of the head as opposed to the bristles, as discussed below).

The head 120 of the oral care implement 100 comprises a front surface 121 and an opposing rear surface 122. A plurality of tooth cleaning elements 123 extend from the front surface 121 of the head 120. In the exemplified embodiment, the tooth cleaning elements 123 are generically illustrated as a block. The exact structure, pattern, orientation and material of the tooth cleaning elements 123 is not to be limiting of the present invention unless so specified in the claims. Thus, as used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 123 of the present invention can be connected to the head 120 in any manner known in the art. For example, staples/anchors, in-mold tufting (IMT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

In the exemplified embodiment, a soft tissue cleanser 124 is positioned on and coupled to the rear surface 122 of the head 120. The soft tissue cleanser 124 comprises a pad portion 126 and a plurality of protuberances 125 protruding from the pad portion 126. In the exemplified embodiment, each of the plurality of protuberances 125 is in the form of a nub. As used herein a "nub" generally refers to a column-like protrusion (without limitation to the cross-sectional shape of the protrusion) which is upstanding from a base surface. In a general sense, the protuberances 125 in the preferred construction have a height that is greater than the width at the base of the protuberance 125 (as measured in the longest direction). Nevertheless, protuberances or nubs could include projections wherein the widths and heights are roughly the same or wherein the heights are somewhat smaller than the base widths. Moreover, in some circumstances (e.g., where the protuberances taper to a tip or include a base portion that narrows to a smaller projection), the base width can be substantially larger than the height.

In one preferred arrangement of the soft tissue cleanser 124, the plurality of protuberances 125 are preferably conically shaped. As used herein, "conically shaped" or "conical" is meant to include true cones, frusto-conically shaped elements, and other shapes that taper to a narrow end and thereby resemble a cone irrespective of whether they are uniform, continuous in their taper, or have rounded cross-sections. In the exemplified embodiment, the soft tissue cleanser 124 including the pad 126 and the protuberances 125 are formed from a resilient material, such as an injection molded thermoplastic elastomer. Without intending to be limited, an example of a suitable elastomeric soft tissue cleanser that may be used with the present invention and positioned on the rear surface 122 of the head 120 is disclosed in U.S. Pat. No. 7,143,462, issued Dec. 5, 2006 to the assignee of the present application, the entirety of which is hereby incorporated by reference. In certain other embodiments, the protuberances 125 of the soft tissue cleanser 124 can take the form of elongated ridges, nubs, or combinations thereof. Furthermore, the invention is not limited to an embodiment that incorporates a soft tissue cleanser 124 on the rear surface 122 of the head 120 and in certain other embodiments the soft tissue cleanser 124 may be omitted.

In the exemplified embodiment, the handle 110 and the head 120 are separately formed components that are operably coupled at a later stage of the manufacturing process by any suitable technique known in the art, including without limitation thermal or ultrasonic welding, a tight-fit assembly, a coupling sleeve, threaded engagement, adhesion, or fasteners. In the exemplified embodiment, the distal region 113 of the handle 110 comprises a plurality of projections 114 that alter the smooth contour of the handle 110 and provide a connection point for a complementarily shaped portion of the head 120. Such protrusions enhance the connection between the handle 110 and the head 120, particularly when such connection is achieved via thermal fusion or ultrasonic welding. Although in the exemplified embodiment the handle 110 and the head 120 are separately formed components, the invention is not to be so limited and in certain other embodiments the head 110 can be formed integrally with the handle 120 as a single unitary structure using a molding, milling, machining or other suitable process.

In certain embodiments, each of the handle 110 and the head 120 are formed of a rigid material, such as for example without limitation polymers and copolymers of ethylene, propylene, butadiene, vinyl compounds and polyesters such as polyethylene terephthalate. Of course, the invention is not to be so limited in all embodiments and in certain other embodiments the handle 110 and/or the head 120 can be formed of other materials. Furthermore, in the exemplified embodiment the end cap 150 is also formed of a rigid material, such as one of the example materials listed above. However, the invention is not to be so limited and the end cap 150 can be formed of other materials, including resilient materials and non-plastic rigid materials such as wood, metal or the like.

In the exemplified embodiment, the handle 110 includes a grip component 115 in a thumb-grip region 116 of the handle 110. The grip component 115 is formed of a resilient material, such as a thermoplastic elastomer, and is coupled to the handle 110 via a technique known in the art such as injection molding or the like. The grip component 115 enhances user comfort when gripping the oral care implement 100 and minimizes or reduces the likelihood of a user's hand slipping on the handle 10 during use of the oral care implement 100 in a wet toothbrushing environment. In the exemplified embodiment, the grip component 115 is only located on a front surface of the handle 110. However, the invention is not to be so limited in all embodiments and in certain other embodiments the grip component 115 may also be positioned on a rear surface and/or along the side surfaces of the handle 110.

The grip component 115 includes a body portion 117 and a plurality of protuberances 118 extending outwardly from the body portion 117. In certain embodiments, the protuberances 118 are nubs extending from the body portion 117 of the grip component 115, such as the nubs discussed above with regard to the soft tissue cleanser 124. Of course, the invention is not to be so limited in all embodiments and the protuberances 118 can take on other shapes and forms such as being columnar protrusions, elongate ridges extending along the width of the body portion 117 of the grip component 115 or the like. The protuberances 118 provide an additional surface for preventing slippage during use of the oral care implement and for enhanced comfort.

In addition to the grip component 115, the handle 110 may be formed with additional resilient materials covering portions of or the entirety of the handle 110 to further enhance the gripability of the handle 110 during use. For example, portions of the handle 110 that are typically gripped by a user's palm during use may be overmolded with a thermoplastic elastomer or other resilient material to further increase comfort to a user. The exact shape, contour and resilient material coverings on the handle 110 are not to be limiting of the present invention unless specifically claimed.

The head 120 of the oral care implement 100 further comprises an applicator 130 located on the rear surface 122 of the head 120. Specifically, the applicator 130 is located on the surface of the head 120 opposite the tooth cleaning elements 123. In certain embodiments, the applicator 130 may be surrounded by or embedded within the soft tissue cleanser 124. Furthermore, in the exemplified embodiment the applicator 130 has projections 131 that are exposed and contact a user's teeth and/or gums during use of the oral care implement 100. The projections 131 are formed integrally with the applicator 130 and follow the contours of the projections 125 of the soft tissue cleanser 124 to further enhance the cleaning of the user's teeth and/or gums.

The head 120 of the oral care implement 100 further comprises a wick member 132 having a first end 133 that is in fluid communication with the oral care fluid 141 contained within the internal reservoir 140 and a second end 134 that is in fluid communication with the applicator 130. The wick member 132 is located within a channel 135 that is formed through the head 120 of the oral care implement 100 from the internal reservoir 140 to the applicator 130. Thus, the channel 135 provides a passageway through the oral care implement 100 from the internal reservoir 140 to the rear surface 122 of the head 120 where the applicator 130 is exposed for contact with a user's teeth and gums during use of the oral care implement 100.

In the exemplified embodiment, the wick member 132 is integrally formed with the applicator 130 out of a capillary material, including without limitation, a fibrous material, ceramic, porous plastic or combinations thereof. Thus, in the exemplified embodiment the oral care fluid 141 in the internal reservoir 140 is delivered to the applicator 130 solely by capillary action through the wick member 132. In certain other embodiments, the applicator 130 and the wick member 132 can be separately formed out of two different types of the capillary materials discussed above. In such embodiments, the oral care fluid 141 may flow through each of the wick member 132 and the applicator 130 at different flow rates depending on the material and capillaries of each component.

For example, the oral care fluid 141 may flow at a faster rate from the internal reservoir 140 onto the wick member 132 than from the wick member 132 onto the applicator 130 to prevent overdosing the oral care fluid 141 onto the user's teeth and/or gums during use of the oral care implement 100. In this manner, the dose of the oral care fluid 141 applied to a user's teeth and/or gums is the amount of oral care fluid 141 saturating the applicator 130. In other words, during use of the oral care implement 100 the oral care fluid 141 on the applicator 130 will become depleted. It will take some amount of time, such as ten minutes, thirty minutes, one hour, two hours or more for the applicator 130 to become re-saturated with the oral care fluid 141. Thus, once the dosage of oral care fluid 141 on the applicator 130 is depleted, the user will not be able to apply more of the oral care fluid 141 onto her teeth and/or gums until the time period has expired and the applicator 130 is again saturated with the oral care fluid 141.

As noted above, the materials that form the applicator 130 and the wick member 132 includes fibrous materials, ceramics and porous plastics, such as those available from Porex Technologies, Atlanta, Ga. One example of a fibrous material is an acrylic material identified as type number C10010, available from Teibow Hanbai Co., Ltd., Tokyo, Japan. A mixture of porous and/or fibrous materials may be provided which have a distribution of larger and smaller capillaries. The applicator 130 and the wick member 132 can be formed from a number of small capillaries that are connected to one another, or as a larger single capillary tube. Furthermore, although delivery of the oral care fluid 141 from the internal reservoir 140 to the applicator 130 is described herein as being accomplished solely by capillary action, in certain other embodiments delivery may be achieved via mechanical action, mechanical pumps and/or electrical pumps or combinations thereof either solely or in addition to the capillary action.

Figure 2:
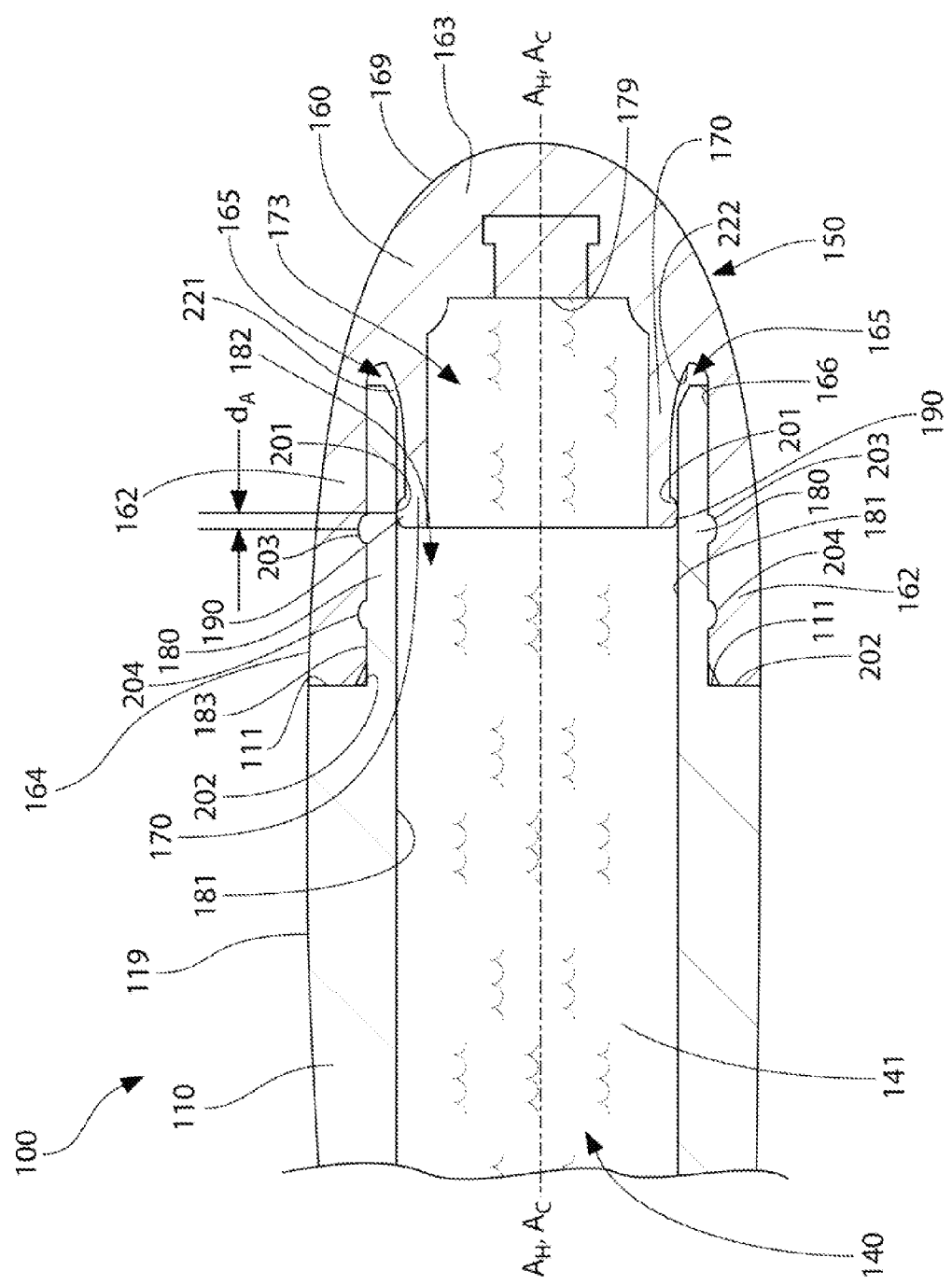
FIG. 2 is a close-up of area II of FIG. 1.
Figure 3:
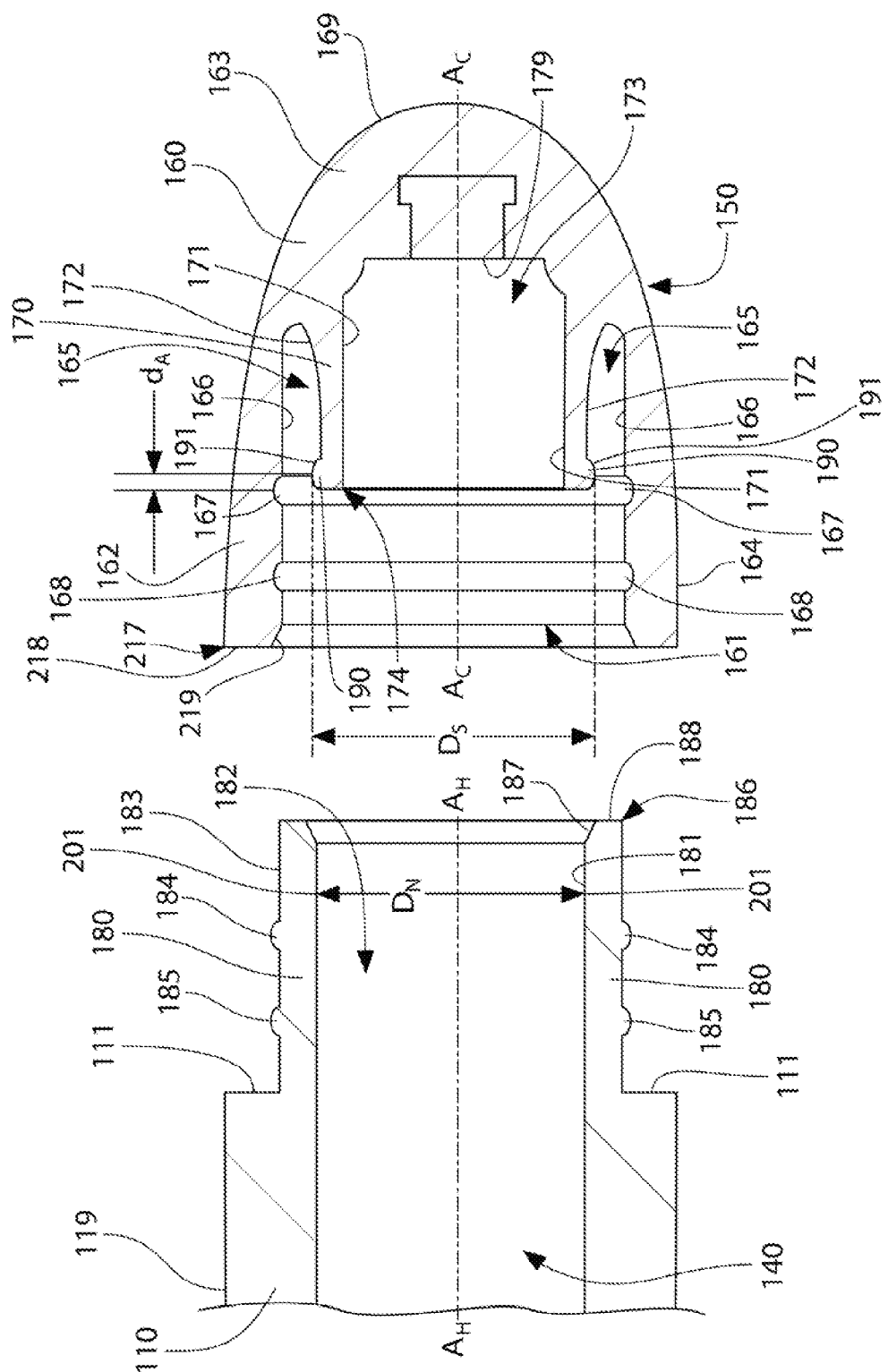
FIG. 3 is an exploded view of the oral care implement of FIG. 2 wherein the end cap is separated from the handle.

Referring to FIGS. 2 and 3 concurrently, the oral care implement 100, and more specifically the details of and connection between the handle 110 and the end cap 150 of the oral care implement 100, will be further described. The oral care implement 100 comprises an annular neck 180 extending from the proximal end 111 of the handle 110. In the exemplified embodiment, the annular neck 180 is integrally formed with the handle 110 as a single unitary component via an injection molding technique or any of the other techniques discussed above. However, the invention is not to be so limited in all embodiments and in certain other embodiments that annular neck 180 can be separately formed from and later connected to the proximal end 111 of the handle 110.

The annular neck 180 comprises an inner surface 181 that defines a passageway 182 into the internal reservoir 140 of the handle 110 and an outer surface 183. Furthermore, the annular neck 180 terminates in a distal edge 186. The distal edge 186 of the annular neck 180 comprises a transverse portion 188 that is oriented transverse to the handle axis $A_H$ and an inner periphery 187. The inner periphery 187 of the distal edge 186 extends between the inner surface 181 of the annular neck 180 and the transverse portion 188 of the distal edge 186. In the exemplified embodiment, the inner periphery 187 of the distal edge 186 is tapered inwardly as it extends from the transverse portion 188 of the distal edge 186 towards the inner surface 181 of the annular neck 180. However, the invention is not to be so limited and in certain other embodiments the inner periphery 187 of the distal edge 186 may be rounded rather than tapered. Tapering or rounding the inner periphery 187 of the distal edge 186 facilitates the coupling of the end cap 150 to the annular neck 180 as will be discussed in more detail below.

In the exemplified embodiment, a second annular seal member 184 and a third annular seal member 185 are integrally formed with the outer surface 183 of the annular neck 180. The second and third annular seal members 184, 185 are annular projections that extend outwardly from the outer surface 183 of the annular neck 180. In the exemplified embodiment, each of the second and third annular seal members 184, 185 has a rounded or dome-shaped outer surface.

Rounding the outer surfaces of the second and third annular seal members 184, 185 facilitates the ability of the end cap 150 to be secured to the annular neck 180 as will be discussed in more detail below. However, the invention is not limited to rounding the outer surfaces of the second and third annular seal members 184, 185 in all embodiments. The second and third annular seal members 184, 185 facilitate the coupling between the annular neck 180 and the end cap 150 and assist in preventing leakage of the oral care fluid 141 from the internal reservoir 140. More specifically, the second and third annular seal members 184, 185 create an interference fit coupling between the annular neck 180 and the end cap 150.

In certain embodiments as will be discussed in detail below, the second and third annular seal members 184, 185 can be formed integrally with the end cap 150 rather than integrally with the annular neck 180. Furthermore, in still other embodiments the second and third annular seal members 184, 185 can be annular gaskets formed of rubber or other elastomeric material that are not integral with either the end cap 150 or the annular neck 180. In certain other embodiments, one or both of the second and third annular seal members 184, 185 may be altogether omitted and coupling of the end cap 150 to the annular neck 180 can be achieved via alternative mechanical means.

The end cap 150 generally comprises a cap body 160 that defines a cap socket 161 and an annular plug wall 170 protruding into the cap socket 161. Furthermore, the cap body 160 comprises an annular wall 162 and an end portion 163, the annular wall 162 having an outer surface 164 and an inner surface 166. In the exemplified embodiment, the end portion 163 of the cap body 160 comprises a dome-shaped outer surface 169 that is substantially flush with the outer surface 164 of the annular wall 162.

In the exemplified embodiment, the annular plug wall 170 is concentric with the annular wall 162 of the cap body 160. Thus, the annular wall 162 of the cap body 160 circumferentially surrounds the annular plug wall 170 about the cap axis $A_C$. The annular wall 162 of the cap body 160 terminates in a distal edge 217 having a transverse portion 218 that is oriented transverse to the cap axis $A_C$ and an inner periphery 219. In the exemplified embodiment, the inner periphery 219 of the distal edge 217 of the annular wall 162 of the cap body 160 is tapered. However, the invention is not to be so limited in all embodiments and in certain other embodiments the inner periphery 219 of the distal edge 217 of the annular wall 162 of the cap body 160 can be rounded. Tapering or rounding the inner periphery 219 of the distal edge 217 of the annular wall 162 facilitates coupling the end cap 150 to the annular neck 180 by providing a ramped surface for the outer surface 183 of the annular neck 180 to ride along during such coupling.

In the exemplified embodiment, the inner surface 166 of the annular wall 162 comprises a first annular groove 167 and a second annular groove 168. Thus, when the end cap 150 is coupled to the annular neck 180, the second and third annular seal members 184, 185 nest within the first and second annular grooves 167, 168 formed into the annular wall 162 of the cap body 160 of the end cap 150. However, the invention is not to be limited by this particular structural arrangement in all embodiments. Thus, as noted above in certain other embodiments the annular neck 180 may comprise the annular grooves and the annular wall 162 of the cap body 160 of the end cap 150 may comprise the second and third annular seal members. In still other embodiments, there may only be a single groove on one of the annular neck 180 or the annular wall 162 of the cap body 160 of the end cap 150 and a single annular seal member on the other one of the annular neck 180 or the annular wall 162 of the cap body 160 of the end cap 150.

The annular plug wall 170 is an annular wall that protrudes from the end portion 163 of the cap body 160 into the cap socket 161. More specifically, the annular plug wall 170 protrudes from a floor 179 of the cap socket 161 and separates the cap socket 161 into a central chamber 173 and an annular chamber 165. Thus, the annular plug wall 170 has an inner surface 171 and an outer surface 172. The inner surface 171 of the annular plug wall 170 defines the central chamber 173. As will be discussed in more detail below, when the end cap 150 is coupled to the annular neck 180, the oral care fluid 141 fills the internal reservoir 140 and the central chamber 173. Due to the projection of the annular plug wall 170 into the cap socket 161, the annular chamber 165 is formed between the outer surface 172 of the annular plug wall 170 and the inner surface 166 of the annular wall 162 of the cap body 160. The annular chamber 165 serves as an additional mechanism for the prevention of leakage of the oral care fluid 141, which will be discussed in more detail below.

A first annular seal member 190 protrudes from the outer surface 172 of the annular plug wall 170. More specifically, the first annular seal member 190 protrudes from the outer surface 172 of the annular plug wall 170 at a distal end 174 of the annular plug wall 170. Furthermore, in the exemplified embodiment the first annular seal member 190 has a distal edge 191 that is rounded about an outer periphery of the distal end 174 of the annular plug wall 170. However, the invention is not to be so limited in all embodiments and in certain other embodiments the distal edge 191 of the first annular seal member 190 may be tapered about an outer periphery of the distal end 174 of the annular plug wall 170. The rounded shape of the distal edge 191 of the first annular seal member 190 in combination with the tapered inner periphery 187 of the distal edge 186 of the annular neck 180 creates relative ramping surfaces to facilitate coupling the end cap 150 to the annular neck 180.

In the exemplified embodiment, the first annular seal member 190 is offset from the first annular groove 167 by an axial distance $d_A$ along the cap axis $A_C$. Furthermore, due to the structural arrangement such that the second annular seal member 184 nests within the first annular groove 167 when the end cap 150 is coupled to the annular neck 180, the first annular seal member 190 is also offset from the second annular seal member 184 by the axial distance $d_A$ along the cap axis $A_C$ when the end cap 150 is coupled to the annular neck 180.

In the exemplified embodiment, the first annular seal member 190 is integrally formed with the annular plug wall 170. Furthermore, the annular plug wall 170 is integrally formed with the rest of the end cap 150 out of a rigid plastic material, such as polypropylene or any of the other rigid plastic materials noted above. Of course, the invention is not to be so limited in all embodiments and the first annular seal member 190 can be a separate component from the annular plug wall 170 in certain other embodiments, such as being a separate gasket that is coupled to the annular plug wall 170.

As noted above, the end cap 150 is coupled to the annular neck 180 by an interference fit. Thus, to couple the end cap 150 to the annular neck 180, the annular neck 180 is inserted into the cap socket 161 in the direction of the handle axis $A_H$ and the cap axis $A_C$. The annular neck 180 is continually inserted until the end cap 150 snaps into place on the annular neck 180 due to the second and third annular seal members 184, 185 nesting within the first and second annular grooves 167, 168. Separating the end cap 150 from the annular neck 180 is achieved in the same manner by pulling on the end cap 150 and the handle 110 in opposite axial directions until the second and third annular seal members 184, 185 are pulled out of the first and second annular grooves 167, 168.

When the end cap 150 is coupled to the handle 110, the passageway 182 from the annular neck 180 into the internal reservoir 140 of the handle 110 is sealed in a fluid-tight manner. Furthermore, when the end cap 150 is coupled to the handle 110 at least a portion of the annular neck 180 extends into the annular chamber 165, the annular plug wall 170 extends into the passageway 182 and the first annular seal member 190 is biased into contact with an annular portion 201 of the inner surface 181 of the annular neck 180. In the exemplified embodiment, a space or gap 221 is left between the distal edge 186 of the annular neck 180 and a floor 222 of the annular chamber 165. However, the invention is not to be so limited in all embodiments and in certain other embodiments the distal edge 186 of the annular neck 180 may contact the floor 222 of the annular chamber 165. Furthermore, when the end cap 150 is coupled to the annular neck 180, the outer surface 183 of the annular neck 180 abuts against the inner surface 166 of the annular wall 162 and the second and third annular seal members 184, 185 nest within the first and second annular grooves 167, 168.

The first annular seal member 190 has an outer diameter $D_S$. Furthermore, the annular portion 201 of the inner surface 181 of the annular neck 180 has an inner diameter $D_N$. Prior to the end cap 150 being coupled to the handle 110, the outer diameter $D_S$ of the first annular seal member 190 is greater than the inner diameter $D_N$ of the annular portion 201 of the inner surface 181 of the annular neck 180. However, when the end cap 150 is coupled to the annular neck 180, the annular plug wall 170 is caused to deflect inwardly towards the central chamber 173 so that the annular neck 180 can fit within the annular chamber 165. More specifically, as the annular neck 180 is inserted into the cap socket 161, the distal edge 186 of the annular neck 180 comes into contact with the first annular seal member 190. Due to the ramped or tapered inner periphery 187 of the distal edge 186S of the annular neck 180 and the rounded or tapered shape of the first annular seal member 190, the first annular seal member 190 will ride against the inner periphery 187 until the annular seal member 190 abuts against the inner surface 181 of the annular neck 180. Thus, the annular neck 180 forces the annular plug wall 170 to deflect inwardly towards the central chamber 173.

Due to the outer diameter $D_S$ of the first annular seal member 190 being greater than the inner diameter $D_N$ of the annular portion 201 of the inner surface 181 of the annular neck 180, the first annular seal member 190 is biased into contact with the annular portion 201 of the inner surface 181 of the annular neck 180 when the annular neck 180 is positioned within the annular chamber 165. More specifically, positioning the annular neck 180 within the annular chamber 165 forces the annular plug wall 170 to deflect inwardly towards the central chamber 173, but the annular plug wall 170 is biased back towards the annular neck 180 due to its desire to maintain its natural orientation (its orientation prior to be coupled to the annular neck 180). Thus, a first annular hermetic seal is formed between the first annular seal member 190 and the annular portion 201 of the inner surface 181 of the annular neck 180 when the end cap 150 is coupled to the annular neck 180 of the handle 110. The first annular seal member 190 provides a constant pressure on the inner surface 181 of the annular neck 180 at the annular portion 201 of the inner surface 181 of the annular neck 180 due to its natural bias.

In the exemplified embodiment, the end cap 150 is coupled to the annular neck 180 of the handle 110 via an interference fit. However, the invention is not to be so limited in all embodiments and in certain other embodiments the end cap 150 can be coupled to the annular neck 180 of the handle 110 via other mechanical connections, such as a coupling sleeve, threaded engagement, adhesion, fasteners or the like.

The proximal end 111 of the handle 110 forms a transverse shoulder 202, which provides a surface for engagement between the proximal end 111 of the handle 110 and the distal edge 217 of the cap body 160. When the end cap 150 is coupled to the annular neck 180 of the handle 110, the distal edge 217 of the cap body 160 is in abutment with the transverse shoulder 202 at the proximal end Ill of the handle. Furthermore, when the end cap 150 is coupled to the annular neck 180 of the handle 110, the outer surface 164 of the annular wall 162 of the cap body 160 is substantially flush with the outer surface 119 of the handle 110. Thus, the outer surface 164 of the annular wall 162 of the cap body 160 of the end cap 150 and the outer surface of the handle 110 form a continuous outer gripping surface of the oral care implement 100.

As discussed above, in the exemplified embodiment when the end cap 150 is coupled to the annular neck 180 of the handle 110, the second annular seal member 184 of the annular neck 180 nests within the first annular groove 167 formed into the annular wall 162 of the cap body 160 and the third annular seal member 185 of the annular neck 180 nests within the second annular groove 168 formed into the annular wall 162 of the cap body 160. The invention is not to be so limited and in certain other embodiments the second and third annular seal members can be formed integrally with the annular wall 162 of the cap body 160 and the first and second annular grooves can be formed into the annular neck 180.

Nonetheless, in the exemplified embodiment the second and third annular seal members 167, 168 are formed integrally with the outer surface 183 of the annular neck 180. The bias of the first annular seal member 190 against the annular portion 201 of the inner surface 181 of the annular neck 180 further biases the second annular seal member 167 into contact with an annular portion 203 of the inner surface 166 of the annular wall 162 of the cap body 160. In the exemplified embodiment, the annular portion 203 of the inner surface 166 of the annular wall 162 of the cap body 160 is located within the first annular groove 167. Thus, a second annular hermetic seal is formed between the second annular seal member 167 and the annular portion 203 of the inner surface 166 of the annular wall 162 of the cap body 160. Similarly, in the exemplified embodiment the bias of the first annular seal member 190 against the annular portion 201 of the inner surface 181 of the annular neck 180 further biases the third annular seal member 168 into contact with a second annular portion 204 of the inner surface 166 of the annular wall 162 of the cap body 160. In the exemplified embodiment, the second annular portion 204 of the inner surface 166 of the annular wall 162 of the cap body 160 is located within the second annular groove 168. Thus, a third annular hermetic seal is formed between the third annular seal member 168 and the second annular portion 204 of the inner surface 166 of the annular wall 162 of the cap body 160.

As a result of the combination of the nesting of the second and third annular seal members 184, 185 within the first and second annular grooves 167, 168 and the biasing of the first annular seal member 190 against the inner surface 181 of the annular neck 180, leaking of the oral care fluid 141 from the internal reservoir 140 is substantially reduced if not eliminated altogether. Specifically, in order for the oral care fluid 141 to leak out of the internal reservoir 140 when the end cap 150 is coupled to the annular neck 180, the oral care fluid 141 would have to first penetrate into the annular chamber 165 by passing through the hermetic seal at the annular portion 201 of the inner surface 181 of the annular neck 180. This is unlikely due to the constant pressure applied onto the inner surface 181 of the annular neck 180 at the annular portion 201 by the first annular seal member 190. Even if the oral care fluid 141 is able to flow into the annular chamber 165, the oral care fluid 141 would then have to flow through the annular portion 203 and the second annular portion 204 of the inner surface 166 of the annular wall 162 of the cap body 160 that is created due to the nesting of the second and third annular seal members 184, 185 within the first and second annular grooves 167, 168. By utilizing several distinct points on the oral care implement 100 as hermetic seals, leakage of the oral care fluid 141 from the internal reservoir 140 is reduced and/or eliminated.

In certain embodiments, the invention can be directed to a method of sealing the passageway 182 leading into the internal reservoir 140 containing the oral care fluid 141 that is located within the handle 110 of the oral care implement or toothbrush 100. In such embodiments, the method may include aligning the end cap 150 with the annular neck 180 which extends from the proximal end 111 of the handle 110 of the toothbrush 100. As discussed above, the end cap 150 comprises the cap body 160 comprising the annular wall 162 and the end portion 163 that collectively define the cap socket 161. The annular neck 180 has the inner surface 181 that defines the passageway 182. Furthermore, the method includes translating the annular neck 18 into the cap socket 161 until each of the following are achieved: (1) the annular plug wall 170 of the end cap 150 extends into the passageway 182; (2) the annular neck 180 extends into the annular chamber 165 formed between the outer surface 172 of the annular plug wall 170 and the inner surface 166 of the annular wall 162 of the cap body 160; and (3) the first annular seal member 190 protruding from the outer surface 172 of the annular plug wall 170 exerts pressure against the annular portion 203 of the inner surface 181 of the annular neck 180, thereby forming a first annular hermetic seal at the annular portion 203.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A toothbrush comprising:
   a handle extending along a handle axis from a proximal end to a distal end, the handle comprising an internal reservoir containing an oral care fluid;
   a head coupled to the distal end of the handle and having a plurality of tooth cleaning elements;
   an annular neck extending from the proximal end of the handle, the annular neck having an inner surface that defines a passageway into the internal reservoir of the handle;
   an end cap comprising:
      a cap body defining a cap socket, the cap body comprising an annular wall and an end portion;
      an annular plug wall having an inner surface defining a central chamber, the annular plug wall protruding from the end portion into the cap socket to form an annular chamber between an outer surface of the annular plug wall and an inner surface of the annular wall of the cap body; and
      a first annular seal member protruding from the outer surface of the annular plug wall; and
   the end cap coupled to the handle to seal the passageway in a fluid-tight manner such that the annular neck extends into the annular chamber, the annular plug wall extends into the passageway, and the first annular seal member biased into contact with an annular portion of the inner surface of the annular neck.

2. The toothbrush according to claim 1 wherein the first annular seal member is integrally formed with the annular plug wall.

3. The toothbrush according to claim 2 wherein the first annular seal member has an outer diameter that is greater than an inner diameter of the annular portion of the inner surface of the annular neck prior to the end cap being coupled to the handle.

4. The toothbrush according to claim 1 wherein a first annular hermetic seal is formed between the first annular seal member and the annular portion of the inner surface of the annular neck.

5. The toothbrush according to claim 1 wherein the annular neck is integrally formed with the handle.

6. The toothbrush according to claim 1 further comprising a second annular seal member between the outer surface of the annular neck and the inner surface of the annular wall of the cap body.

7. The toothbrush according to claim 6 wherein the first and second annular seal members are offset from one another by an axial distance along a cap axis.

8. The toothbrush according to claim 6 wherein the second annular seal member is integrally formed with one of the outer surface of the annular neck or the inner surface of the annular wall of the cap body, and wherein the other one of the outer surface of the annular neck or the inner surface of the annular wall of the cap body comprises a first annular groove, the second annular seal member nesting within the first annular groove.

9. The toothbrush according to claim 6 wherein the second annular seal member is integrally formed with the outer surface of the annular neck, and wherein the bias of the first annular seal member against the annular portion of the inner surface of the annular neck biases the second annular seal member into contact with an annular portion of the inner surface of the annular wall of the cap body; and wherein a second annular hermetic seal is formed between the second annular seal member and the annular portion of the inner surface of the annular wall of the cap body.

10. The toothbrush according to claim 1 wherein the annular plug wall is concentric with the annular wall of the cap body.

11. The toothbrush according to claim 1 wherein the first annular seal member is located at a distal end of the annular plug wall.

12. The toothbrush according to claim 11 wherein the first annular seal member has a distal edge that is tapered or rounded about an outer periphery of the distal end of the annular plug wall.

13. The toothbrush according to claim 1 further comprising:
   an applicator located on a side of the head opposite the plurality of tooth cleaning elements;
   a wick member having a first end in fluid communication with the oral care fluid in the internal reservoir and a second end in fluid communication with the applicator; and
   wherein the oral care fluid in the internal reservoir is delivered to the applicator solely by capillary action through the wick member.

14. The toothbrush according to claim 1, wherein the central chamber of the cap is in fluid communication with the internal reservoir of the handle such that fluid in the internal reservoir also fills the central chamber.

15. A toothbrush comprising:
   a handle extending along a handle axis from a proximal end to a distal end, the handle comprising an internal reservoir containing an oral care fluid;
   a head coupled to the distal end of the handle and having a plurality of tooth cleaning elements;
   an annular neck extending from the proximal end of the handle, the annular neck having an inner surface that defines a passageway into the internal reservoir of the handle;
   an end cap comprising:

a cap body defining a cap socket, the cap body comprising an annular wall and an end portion;

a plug protruding from the end portion into the cap socket to form an annular chamber between an outer surface of the plug and an inner surface of the annular wall of the cap body; and a first annular seal member between the outer surface of the plug and the inner surface of the annular wall of the cap body; and the end cap coupled to the handle to seal the passageway in a fluid-tight manner such that the annular neck extends into the annular chamber, the plug extends into the passageway, and the first annular seal member exerting pressure against an annular portion of the inner surface of the annular neck.

16. The toothbrush according to claim 15 further comprising a second annular seal member between the outer surface of the annular neck and the inner surface of the annular wall of the cap body, the first and second annular seal members being offset from one another by an axial distance along a cap axis.

17. The toothbrush according to claim 16 wherein the second annular seal member is integrally formed with the outer surface of the annular neck, and wherein the pressure exerted by the first annular seal member against the annular portion of the inner surface of the annular neck causes the second annular seal member to exert pressure against an annular portion of the inner surface of the annular wall of the cap body.

18. The toothbrush according to claim 15 wherein the first annular seal member is integrally formed with the plug, and wherein the first annular seal member has an outer diameter that is greater than an inner diameter of the annular portion of the inner surface of the annular neck prior to the end cap being coupled to the handle.

19. The toothbrush according to claim 15 wherein the annular wall of the cap body terminates in a distal edge, the distal edge being in abutment with a transverse shoulder at the proximal end of the handle, the annular wall of the cap body having an outer surface that is substantially flush with an outer surface of the handle, and wherein the end portion of the cap body comprises a dome-shaped outer surface that is substantially flush with the outer surface of the annular wall of the cap body.

20. A method of sealing a passageway leading into an internal reservoir containing an oral care fluid that is located within a handle of a toothbrush, the method comprising:
  a) aligning an end cap with an annular neck extending from a proximal end of the handle of the toothbrush, the end cap comprising a cap body comprising an annular wall and an end portion that collectively define a cap socket, the annular neck having an inner surface that defines the passageway; and
  b) translating the annular neck into the cap socket until: (1) a plug of the end cap extends into the passageway; (2) the annular neck extends into an annular chamber formed between an outer surface of the plug and an inner surface of the annular wall of the cap body; and (3) a first annular seal member protruding from the outer surface of the plug exerts pressure against an annular portion of the inner surface of the annular neck, thereby forming a first annular hermetic seal.

* * * * *